(12) United States Patent
Ng et al.

(10) Patent No.: US 10,912,537 B2
(45) Date of Patent: Feb. 9, 2021

(54) IMAGE REGISTRATION AND GUIDANCE USING CONCURRENT X-PLANE IMAGING

(71) Applicant: KONINKLIJKE PHILIPS N.V., Eindhoven (NL)

(72) Inventors: Gary Cheng-How Ng, Redmond, WA (US); Thomas Shu Yin Tang, Richmond Hill (CA); Gladys Tsz Ling Chan, Richmond Hill (CA)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 409 days.

(21) Appl. No.: 15/118,217

(22) PCT Filed: Feb. 9, 2015

(86) PCT No.: PCT/IB2015/050948
§ 371 (c)(1),
(2) Date: Aug. 11, 2016

(87) PCT Pub. No.: WO2015/136392
PCT Pub. Date: Sep. 17, 2015

(65) Prior Publication Data
US 2017/0164931 A1    Jun. 15, 2017

Related U.S. Application Data

(60) Provisional application No. 61/950,880, filed on Mar. 11, 2014.

(51) Int. Cl.
*A61B 8/08*    (2006.01)
*A61B 8/00*    (2006.01)
(Continued)

(52) U.S. Cl.
CPC ............ *A61B 8/5261* (2013.01); *A61B 5/055* (2013.01); *A61B 6/025* (2013.01); *A61B 6/032* (2013.01);
(Continued)

(58) Field of Classification Search
CPC ......... A61B 8/5261; A61B 8/54; A61B 6/025; A61B 6/032; A61B 6/037; A61B 5/055;
(Continued)

(56) References Cited

U.S. PATENT DOCUMENTS 8,731,264 B2   5/2014   Kruecker et al.
9,600,856 B2   3/2017   Bzdusek et al.
(Continued)

FOREIGN PATENT DOCUMENTS

EP    1933278 A1    6/2008
JP    2007244575 A    9/2007
(Continued)

OTHER PUBLICATIONS

Huber et al., "Oblique Magnetic Resonance Imaging of Normal Structures", AJR 145:843-846, Oct. 1985 (Year: 1985).*
(Continued)

*Primary Examiner* — Bill Thomson
*Assistant Examiner* — Aminah Asghar

(57) ABSTRACT

A system for image alignment includes an alignment mechanism (132) configured to permit user alignment of images. A first imaging modality (110) is configured to concurrently provide images in two imaging planes using an imaging mechanism (134) associated with the alignment mechanism (132). An image processing module (126) is configured to display first images collected with the first imaging modality and second images collected with a second imaging modality (130) to permit user alignment using the alignment mechanism between the first images and the second images
(Continued)

in multiple planes. A registration module (115) is stored in memory and configured to register the first images with corresponding second images in the multiple planes when alignment in the multiple planes has been achieved.

19 Claims, 7 Drawing Sheets

(51) Int. Cl.
*A61B 5/055* (2006.01)
*A61B 6/02* (2006.01)
*A61B 6/03* (2006.01)
*A61B 6/00* (2006.01)

(52) U.S. Cl.
CPC ............ *A61B 6/037* (2013.01); *A61B 8/0841* (2013.01); *A61B 8/463* (2013.01); *A61B 8/467* (2013.01); *A61B 8/483* (2013.01); *A61B 8/5246* (2013.01); *A61B 8/54* (2013.01); *A61B 6/5235* (2013.01); *A61B 8/4245* (2013.01)

(58) Field of Classification Search
CPC ....... A61B 8/5246; A61B 8/483; A61B 8/467; A61B 8/463; A61B 8/0841; A61B 8/4245; A61B 6/5235; A61B 5/06; A61B 2034/107; G06T 7/0012; G06T 5/50; G06T 3/0068; G06T 7/30
See application file for complete search history.

(56) References Cited

U.S. PATENT DOCUMENTS

| | | | |
|---|---|---|---|
| 2003/0135119 A1* | 7/2003 | Lee ................... | A61B 8/0833 600/461 |
| 2006/0020204 A1 | 1/2006 | Serra et al. | |
| 2006/0072808 A1* | 4/2006 | Grimm ................ | A61B 8/4254 382/151 |
| 2008/0247506 A1 | 10/2008 | Maschke | |
| 2012/0059260 A1* | 3/2012 | Robinson ............ | A61B 8/0841 600/439 |
| 2013/0231559 A1 | 9/2013 | Hyun et al. | |
| 2014/0135623 A1* | 5/2014 | Manak ................. | A61B 8/4416 600/427 |
| 2015/0110373 A1* | 4/2015 | Shaham ................ | G06T 7/0012 382/131 |

FOREIGN PATENT DOCUMENTS

| | | |
|---|---|---|
| JP | 2011167330 A | 9/2011 |
| WO | 2005083629 A1 | 9/2005 |
| WO | 2011063517 A1 | 6/2011 |
| WO | 2013179224 A1 | 12/2013 |

OTHER PUBLICATIONS

Lindseth et al., "Multimodal image fusion in ultrasound-based neuronavigation: improving overview and interpretation by integrating preoperative MRI with intraoperative 3D ultrasound", Computer Aided Surgery, Taylor & Francis Inc., vol. 8, No. 2, Jan. 2, 2003, pp. 46-69.

* cited by examiner

IMAGE REGISTRATION AND GUIDANCE USING CONCURRENT X-PLANE IMAGING

This application is the U.S. National Phase application under 35 U.S.C. § 371 of International Application No. PCT/M2015/050948, filed on Feb. 9, 2015, which claims the benefit of U.S. Provisional Application Ser. No. 61/950,880, filed Mar. 11, 2014. These applications are hereby incorporated by reference herein.

BACKGROUND

Technical Field

This disclosure relates to medical instruments and more particularly to imaging systems and methods, which employ multiple planes for image registration and guidance for medical devices.

Description of the Related Art

Image fusion relates to the process of reformatting and displaying an image slice through a volume data set (e.g., computed tomography (CT) or magnetic resonance (MR)) that corresponds with a scan plane of a live ultrasound image. The reformatted CT can be overlaid either on the live ultrasound image or shown in a side-by-side format. CT provides better lesion visualization for some tumors as compared with ultrasound. Ultrasound provides a live image whereas the CT represents a static snapshot of a patient's anatomy. One advantage of image fusion is that image fusion provides the advantages of both modalities. For example, the good lesion visualization from a CT is provided with the live information and feedback from an ultrasound when the two modalities are fused. Image fusion can be employed to target small lesions that are poorly visualized in live ultrasound.

For image fusion to be possible, the ultrasound images need to be registered to the CT images. Registration is the correlation of spatial locations in the CT images to the same spatial locations in the ultrasound images. Many registration techniques exist. One method is called plane registration. In this method, the ultrasound probe is held perpendicular to the patient's body to get an ultrasound scan plane parallel to an axial CT acquisition slice. A common anatomical point is then marked in the CT and in the ultrasound. This combination of a common plane and a common point is sufficient to register the CT image to the ultrasound image.

Conventional probes generate a single scan plane along an azimuthal plane. Conventional registration with conventional transducers may employ a manual plane match, which is fast but prone to errors due to probe angle in the sagittal (non-imaged) plane. In addition, conventional probes can only show one plane through a targeted lesion, and frequently, even though the scan plane appears to be going through a center of a targeted lesion, partial volume effects can result in the scan plane being off-center. Consequences may include imprecise needle placement for biopsies and procedures or other errors.

SUMMARY

In accordance with the present principles, a system for image alignment includes an alignment mechanism configured to permit user alignment of images. A first imaging modality is configured to concurrently provide images in two or more imaging planes. An image processing module is configured to display first images collected with the first imaging modality and second images collected with a second imaging modality to permit user alignment using the alignment mechanism between the first images and the second images in multiple planes. A registration module is stored in memory and configured to register the first images with corresponding second images in the multiple planes when alignment in the multiple planes has been achieved. A system for procedure guidance includes multiple planes of fused images, and the multiple plane displays are used for procedure guidance.

A system for image alignment includes an alignment mechanism configured to permit user alignment of images. A first imaging modality is configured to concurrently provide images in two imaging planes using an imaging mechanism associated with the alignment mechanism. An image processing module is configured to display first images collected with the first imaging modality and second images collected with a second imaging modality to permit user alignment using the alignment mechanism between the first images and the second images in multiple planes. A registration module is stored in memory and configured to register the first images with corresponding second images in the multiple planes when alignment in the multiple planes has been achieved.

Another system for image alignment includes first images taken in real-time by a first imaging modality and second images taken using a second imaging modality. A probe associated with the first imaging modality is configured to concurrently provide images in at least two imaging planes corresponding with imaging planes of the second images. An image processing module is configured to display the first images and the second images on each of the at least two planes to permit user alignment between the first images and the second images in multiple planes by manipulation of the probe. A registration module is stored in memory and configured to register the first images with corresponding second images in the at least two planes when alignment in the multiple planes has been achieved.

A method for image alignment includes positioning an alignment mechanism associated with a first imaging modality to concurrently provide images in at least two imaging planes for a subject; processing first images collected with the first imaging modality and second images collected with a second imaging modality to permit user alignment between the first images and the second images in multiple planes; visually aligning corresponding first and second images in the multiple planes using the alignment mechanism; and locking in the alignment of the first images with corresponding second images in the multiple planes when visual alignment in the multiple planes has been achieved.

Another method for instrument guidance includes acquiring real-time images with a first modality in at least two imaging planes; fusing the real-time images with second images collected with a second imaging modality that correspond to the real-time images in the at least two imaging planes to generate fused images; and guiding an instrument by concurrently visualizing the fused images in the at least two imaging planes to position the instrument during a procedure.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
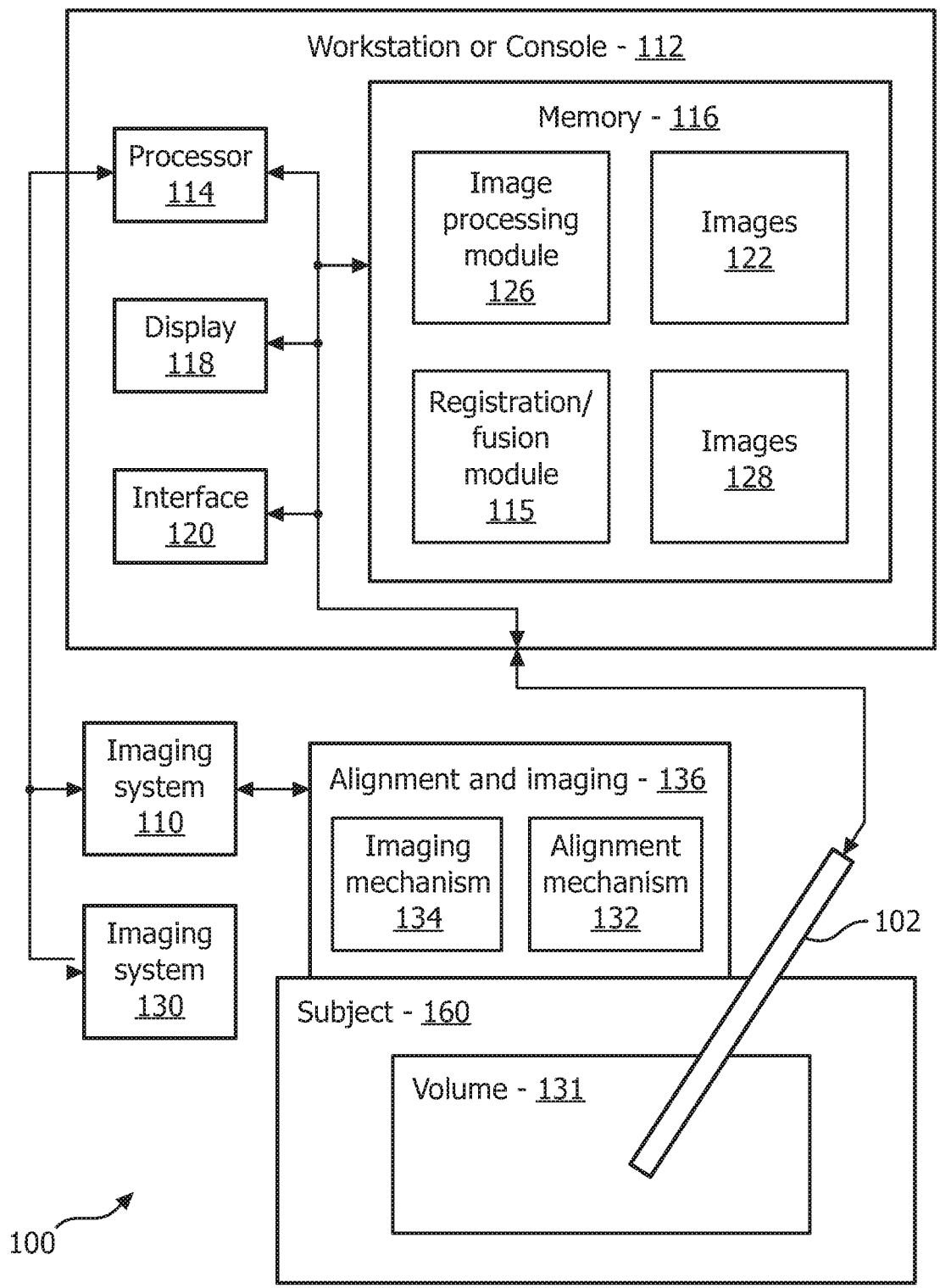
FIG. 1 is a block/flow diagram showing a system for image registration and medical device guidance in accordance with illustrative embodiments.

In accordance with the present principles, systems and methods are provided for fusing images based on multi-plane registrations. In one embodiment, an imaging and alignment mechanism or feature, e.g., an electronic three-dimensional (3D) probe, may be employed to generate live X-planes for alignment and simultaneous image fusion, registration and display in multiple planes. The electronic 3D probe is capable of generating orthogonal X-planes, multi-planar renderings (MPRs) or even any arbitrary slice through a volume. In accordance with some embodiments, real-time images (e.g., ultrasound, x-ray, etc.) may be registered with static images (e.g., computed tomography (CT), magnetic resonance (MR), positron emission tomography (PET), single photon emission computed tomography (SPECT), cone-beam CT, tomosynthesis, prior ultrasound volume, etc.). The static images usually include greater accuracy or other benefits over the real-time (live) images.

The present principles may be employed in image alignment, image fusion/registration and instrument guidance using the multi-plane visualization. Concurrent live imaging with orthogonal planes with an electronic 3D probe provides visualization of at least two planes and permits a user an opportunity to correct for any errors in multiple planes. Similarly, this concept may be used to provide improved accuracy in marking target locations and needle guidance to a center of a tumor or other point of interest since a pair of orthogonal live image planes fused with their respective static plane images will provide more definitive visualization of a true center of a lesion or the point of interest. In one embodiment, electronic 3D probes display multiple planes concurrently and may be employed to show proper needle placement or other device placement, e.g., in the center of the lesion or point of interest.

Once registration has successfully occurred, concurrent X-plane imaging may be employed to display simultaneous fused images in multiple planes. This could be advantageous for procedure guidance since true visualization of the center of a lesion can be achieved, and improved certainty of the needle tip position with a lesion can be obtained. A system is described herein for procedure guidance where multiple planes (e.g., orthogonal planes) of live ultrasound are fused with the corresponding CT slice and these multiple displays of the planes are used for procedure guidance.

It should be understood that the present invention will be described in terms of instruments for medical imaging and alignment; however, the teachings of the present invention are much broader and are applicable to imaging of any system including mechanical systems, anatomical models, machinery, pipe systems, etc. In some embodiments, the present principles are employed in imaging or analyzing complex biological or mechanical systems. In particular, the present principles are applicable to internal imaging procedures for biological systems and procedures in all areas of the body such as the heart, gastro-intestinal tract, excretory organs, blood vessels, etc.

The elements depicted in the FIGS. may be implemented in various combinations of hardware and software and provide functions, which may be combined in a single element or multiple elements. The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes, which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk read only memory (CD-ROM), compact disk read/write (CD-R/W), Blu-Ray™ and DVD.

Referring now to the drawings in which like numerals represent the same or similar elements and initially to FIG. 1, a system 100 for imaging, image alignment, registration and device guidance is illustratively shown in accordance with particularly useful embodiments. System 100 may include a workstation or console 112 from which a procedure is supervised and/or managed. Workstation 112 preferably includes one or more processors 114 and memory 116 for storing programs and applications. Memory 116 may store an image registration or fusion module 115 configured to fuse or register two or more images from two or more images or imaging modalities. The imaging modalities preferably include a real-time (live) imaging modality 110, such as ultrasound, and a more accurate or static imaging modality 130, such as, e.g., computed tomography (CT), magnetic resonance (MR), positron emission tomography (PET), single photon emission computed tomography (SPECT), cone-beam CT, tomosynthesis, prior ultrasound volume, etc.

While the present principles contemplate two imaging modalities, a greater number of imaging modalities may be employed or multiples of a same imaging modality or any combination of imaging modalities may be employed. In addition, while multiple real-time imaging modalities 110 may be employed together, the more accurate or static imaging modality or modalities 130 may be performed or collected in advance of the real-time imaging modality 110. The static imaging modalities may be part of the system 100 or may be part of another system (not shown) and images 128 of the static imaging modalities are provided to and stored in the memory 116. The images 128 collected and stored in memory 116 may be employed for use by the registration/fusion module 115 and/or an image processing module 126.

System 100 may be employed for guidance of a medical device 102. The medical device 102 may include a needle, a catheter, a guidewire, a probe, an endoscope, a robot, an electrode, a filter device, a balloon device, or other medical component, etc. The medical device 102 may be guided into a volume 131 or point of interest in a subject 160 (e.g., a patient).

In particularly useful embodiments, an imaging mechanism 134 is provided for use with the real-time imaging modality 110 (e.g., ultrasonic imaging). This imaging mechanism 134 may include an electronic three-dimensional (3D) probe or 3D ultrasound transducer probe, which provides concurrent imaging in at least two planes. The probe 134 may include a two-dimensional (2D) array transducer that can generate, e.g., scan planes along the azimuth (horizontal) and the elevation (vertical) dimensions. 2D array transducers, such as matrix transducers, are generally known in the art, and can be employed for 3D ultrasound volume imaging. This imaging mechanism 134 is coupled to an alignment interface or mechanism 132, which permits the user to line up the image from the live modality with the image from the static modality (or other image combinations). This alignment mechanism 132 can take various forms including a track ball, joystick, dial, etc., which permit the alignment of fused images in multiple planes. The alignment mechanism 132 and the imaging mechanism 134 may be integrated in one unit (e.g., apparatus 136). For example, the ultrasound probe itself can be employed as the imaging mechanism 134 and the alignment mechanism 132, where the pitch and yaw of the probe serves to modify the alignment of the respective modalities.

The alignment mechanism 132 and imaging mechanism 134 can be described collectively in terms of an alignment and imaging apparatus (apparatus) 136. In a particularly useful embodiment, the apparatus 136 includes an electronic 3D probe that is capable of acquiring and displaying live ultrasound images in multiple planes with arbitrary orientations and aligning these images for registration and guidance applications. The 3D probe is capable of functioning as a three-dimensional mouse to move images for alignment. In this way, the 3D probe functions as both the imaging mechanism 134 and the alignment mechanism 132 and acquires and displays multi-planar live ultrasound images, which provides more certainty for lesion position determination relative to surrounding anatomy, and facilitates alignment of the images for more accurate registration and safer guidance of needles to a lesion or other regions of interest. The 3D probe is capable of acquiring a live volume of ultrasound data. The volume of ultrasound data could be rendered and used to visualize surfaces of organs and allow planning of approaches to these organs, or to lesions located inside the organs.

Workstation 112 includes a display 118 for viewing internal images 122, 128 of a subject (patient) or volume 131 and may include the images 122, 128 that are overlays, fused or otherwise registered between different imaging modalities. Images 122 are preferably live or real-times images, while images 128 are preferably static or higher resolution/accurate images. Images 122 and 128 preferably include images taken from a common vantage point (planes) so that the images can be registered and/or fused.

The display or displays 118 are provided to give a user visual feedback for aligning image planes of the two or more imaging modalities. Display 118 may also permit a user to interact with the workstation 112 and its components and functions, or any other element within the system 100. This is further facilitated by an interface 120, which may include a keyboard, mouse, a joystick, a haptic device, or any other peripheral or control to permit user feedback from and interaction with the workstation 112. Interface 120 and alignment mechanism 132 may be integrated or may be separate features.

In particularly useful embodiments, the electronic 3D probe (134) is employed to generate live concurrent orthogonal planes of ultrasound or other real-time imaging modality (110) for registering with static (e.g., CT, MR, etc.) data sets (more accurate and/or static imaging modality 130) that are sliced in similar planes. Orthogonal X-planes may be employed to generate live fusion overlay views (e.g., CT or MR plus ultrasound) on the display 118 that can provide very accurate tracking of, e.g., needle placement in lesions or other instrument placements, and assist in mitigating ultrasound induced inaccuracies, such as, partial volume effects, the impact of out of plane targets, etc.

In one embodiment, Digital Imaging and Communications in Medicine (DICOM) header information may be employed for imaging modalities 130 (e.g. CT or MR) to determine how to generate the ultrasound planes for use in registration with the imaging modality 110. The image processing module 126 reads the acquisition angle (e.g., DICOM header information) from the images 128 and can make a correction in the live images 122. In addition, during use, images 122 and 128 in multiple corresponding planes may be concurrently visualized to permit a user to perform an alignment function, e.g., between two orthogonal planes to ensure proper image alignment before locking in a registration position by the registration module 115.

It should be understood that instead of providing live X-planes from the 3D probe 134, a volume acquisition could be acquired for real-time imaging modality 110. Plane registration may then be accomplished by the registration module 115 by selecting the appropriate plane(s) from the volume (e.g., a 3D ultrasound volume) that line up with the images from the other previously acquired imaging modality 130 (e.g., CT slices). In addition, instead of using the X-planes during registration, the live X-plane may be provided after the ultrasound is fused to the CT. In this way, the live image will have an exact match up to the fused image, which already includes a version of the image (a previously taken live image). This will make user manipulation and alignment even more accurate. This alignment is preferably performed manually using multiple planes of fused images. The alignment includes visual feedback from the display images to concurrently align images in multiple planes.

In another embodiment, common points may be selected or assigned in the images to permit visual alignment by the operator. For example, the operator may click on a common point, using the alignment mechanism 132 (or interface 120), between an ultrasound image approximately parallel to the axial CT plane, and an axial CT image, and then click on a common point between an ultrasound image approximately parallel to the sagittal CT plane and a sagittal slice through the CT volume. Selecting common points in the sagittal orientation allows the system 100, to compensate for any tilt should the initial ultrasound plane not be exactly parallel to the axial CT acquisition plane. This is what the user is expected to do currently by looking at an overlay image of ultrasound on the CT (or MR), and adjusting the ultrasound plane such that the similarity between the two modalities is maximized. However, to get the ultrasound scan plane completely parallel to the CT acquisition plane is very difficult in actual practice when looking at a single plane. The embodiments described here achieve results with much greater positional certainly due to simultaneous visualization of the ultrasound and CT overlay in two or more planes.

For example, when two orthogonal planes are acquired in live ultrasound, along with two orthogonal slices generated from the CT volume, there are several ways for aligning the ultrasound planes to the CT planes. One way is by overlaying the CT planes on top of the live ultrasound planes, and using the probe position adjustment to align the CT to the ultrasound. Another way includes selecting using the user interface 120 (e.g., mouse clicking, etc.) on common points in the CT plane and/or the ultrasound plane, and associating these points with each other (e.g., concurrently aligning corresponding points in each of multiple image planes").

The system 100 may be employed to identify whether the imaging modality (130) (e.g., CT or MR) dataset has a non-zero acquisition angle (e.g., oblique acquisition). This value can be read and propagated to the 3D probe 134. The axial and sagittal planes of the live ultrasound have the oblique angle applied to their images by the image processing module 126 or by the registration module 115. The user then proceeds to align the planes visually and then lock in the registration once multi-planar alignment is achieved, as described.

Figure 2:
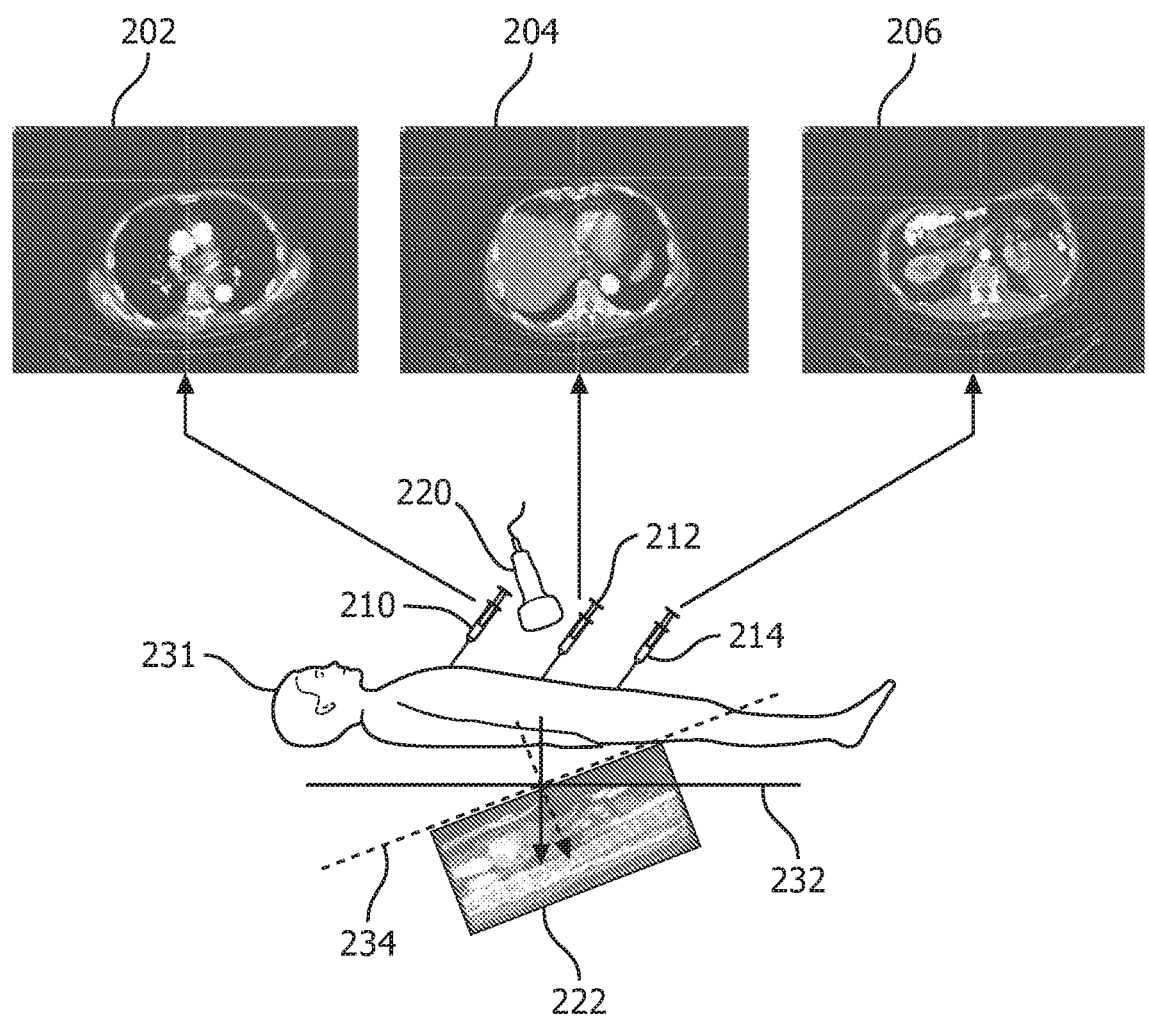
FIG. 2 is a diagram showing image alignment errors corrected in accordance with the present principles.

Referring to FIG. 2, a diagram shows an example of plane registration misalignment error. Images 202, 204 and 206 depict CT cross-sections taken perpendicularly to an axial direction (e.g., sagittal plane) of a patient 231 at locations 210, 212 and 214, respectively. A sagittal slice 222 through the use of CT is depicted for reference. An ultrasonic probe 220 is employed to obtain ultrasonic images in real-time. While conventional plane registration can be accomplished rapidly, it is prone to errors and may not be usable with CT or MR acquisitions (202, 204 and 206) away from the plane where the registration is performed (212) on the patient 231. This is because a small angular error in the ultrasound transducer when defining the axial plane results in increasing spatial mismatch the further one goes away from the registration location (212).

For small parts and musculoskeletal (MSK) imaging, for example, MR acquisitions are typically done in an oblique orientation. As such, even if the operator takes care to ensure that the ultrasound probe is perpendicular to the patient's position, alignment between the ultrasound plane and the acquisition plane of the MR may not be achieved.

Assuming an axial CT is acquired for the patient 231, the user has to hold the ultrasound probe 220 to provide a scan plane that is parallel to an axial plane 232 (or perpendicular to the patient's body) when scanning the patient. Any deviations from parallel result in increasing registration errors when going further away from the registration location, that is, traveling along a rotated axial plane 234 corresponding with the orientation of the probe 220. A small deviation from being perfectly perpendicular to the patient's body is very difficult to detect visually, especially since the abdomen is a curved surface.

At the point of registration, a middle slice 204 at the position 212 of the CT relative to the ultrasound probe 220 is correct. An overlay of the live ultrasound image onto the prior CT shows perfect alignment. However, because the ultrasound probe was slightly tilted during the plane registration, this effectively tilts the CT images 202 and 206 by the same amount relative to the physical position of the patient 231. Towards the foot of the patient, any ultrasound scans overlaid onto the CT will be several centimeters lower (posterior direction) than the corresponding CT image. The opposite happens towards the head. An ultrasound scan shows up several centimeters above (anterior direction) the corresponding CT image. If an electromagnetically (EM) tracked needle is used at the same time for the procedure, estimates of the needle tip via EM tracking relative to the CT will exhibit the same error. The cross-hair lines in the images 202, 204 and 206 show the needle tip position relative to the respective image. This registration error inaccuracy has an impact on the confidence of a user that a location where they are placing a needle in using ultrasound is the exact same location shown in the CT image.

Referring again to FIG. 1, the imaging mechanism 134 provides live ultrasound images 122 in both an axial plane and a sagittal plane (or other sets of orthogonal or non-orthogonal planes). Plane alignment is performed for images 128 of the second imaging modality (e.g., CT, MR, etc.) to images 122 of the first imaging modality (e.g., ultrasound). Concurrent visualization of the images 122 and 128 in multiple planes immediately highlights any tilt in the alignment. This tilt is visualized and corrected immediately by, e.g., adjusting the alignment mechanism 132 until the sagittal planes of the ultrasound (122) and CT (128) are aligned. Aside from a tilt, if there were any error in the head-toe direction, the sagittal plane would highlight that offset and allow the user to correct for it.

Instead of or in addition to the sagittal plane, the coronal plane may be employed as well. A concurrent live ultrasound plane could be generated in the coronal dimension that could be used to identify and correct for errors in alignment in that orientation. Other plane orientations are also contemplated.

For MR or CT acquisitions that are oblique, the angle of the oblique acquisition is stored in the DICOM header. That value could be read by the ultrasound or other real-time imaging system, and applied to the acquisition of the X-planes such that the X-planes have that same oblique angle applied. This ensures that a clinical user could follow a consistent protocol for registration ("always place your probe perpendicular to the patient") instead of having to take into account the orientation of the CT or MR acquisition from patient to patient.

The present principles may employ one or more additional planes to not only eliminate registration and angle errors but also provide improved targeting of points of interest (e.g., lesions). One purpose of image fusion and navigation is to enable very precise targeting (tool guidance) of, e.g., lesions using image data from multiple modalities. In addition, other tracking technologies may be employed, e.g., electromagnetic (EM) tracking information may be used for the needles in addition to ultrasound guidance. However, with a conventional probe, since only one plane is provided, what frequently looks like a center of the lesion is actually off-center in another plane.

Figure 3A:
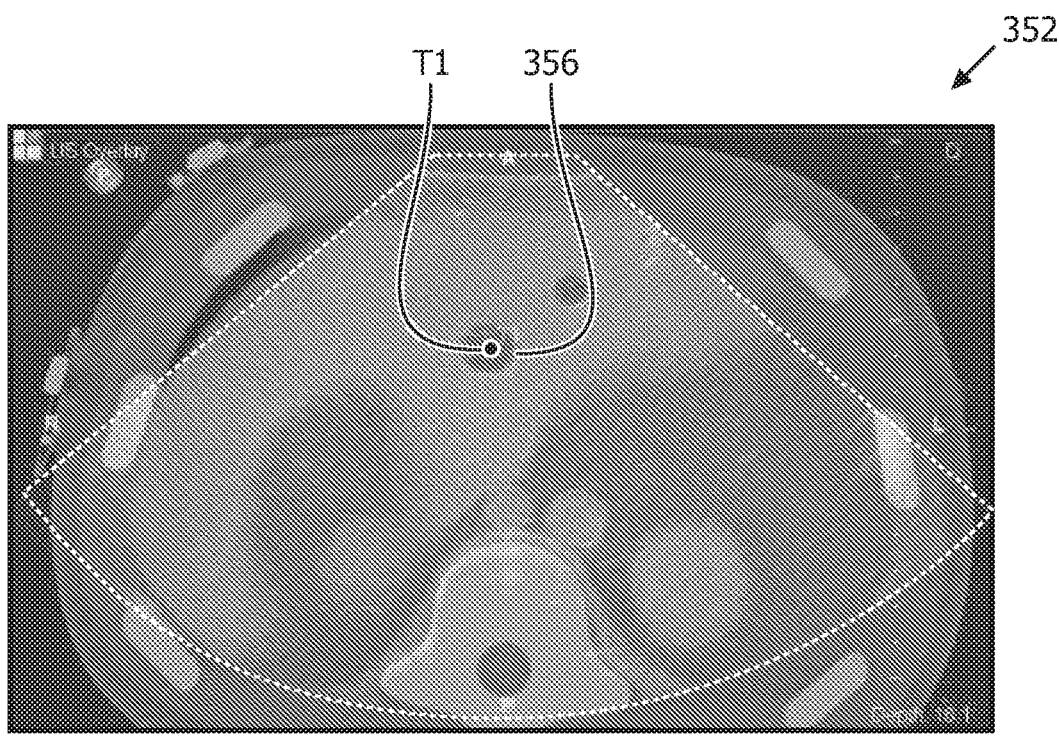
FIG. 3A is an image showing a first image plane of a lesion that appears to be marked at its center.

Referring to FIG. 3A, an image 352 is shown having a CT image fused with an ultrasound image in an axial plane. The scan plane of the ultrasound and the reformatted CT appear to be going through the center of a large lesion, and that location is then marked with T1.

Figure 3B:
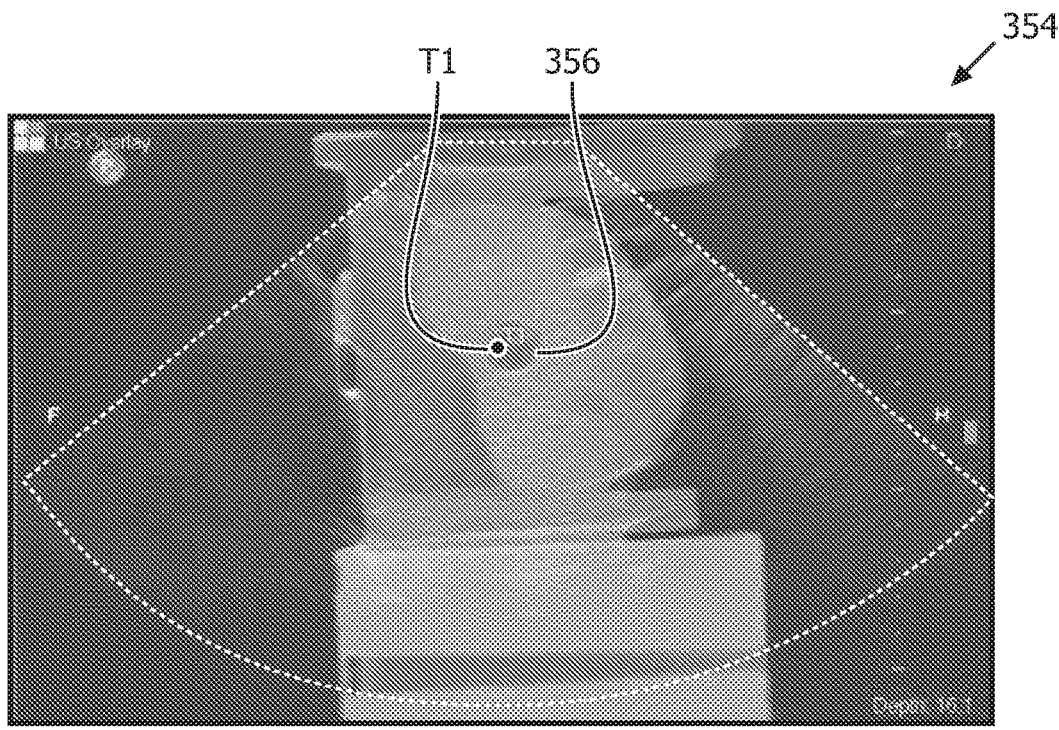
FIG. 3B is an image showing a second image plane orthogonal to the first image plane of FIG. 3A showing the marked center offset from the center position.

Referring to FIG. 3B, when the probe is rotated physically in another direction to view the sagittal plane, T1 in an image 354 is located significantly off-center such that T1 is not actually in the middle of a lesion 356. This error is corrected by providing real-time image tracking of multiple planes concurrently as described. The present principles provide for improved guidance accuracy, by employing multiple plane visualizations of common features.

Figure 4:
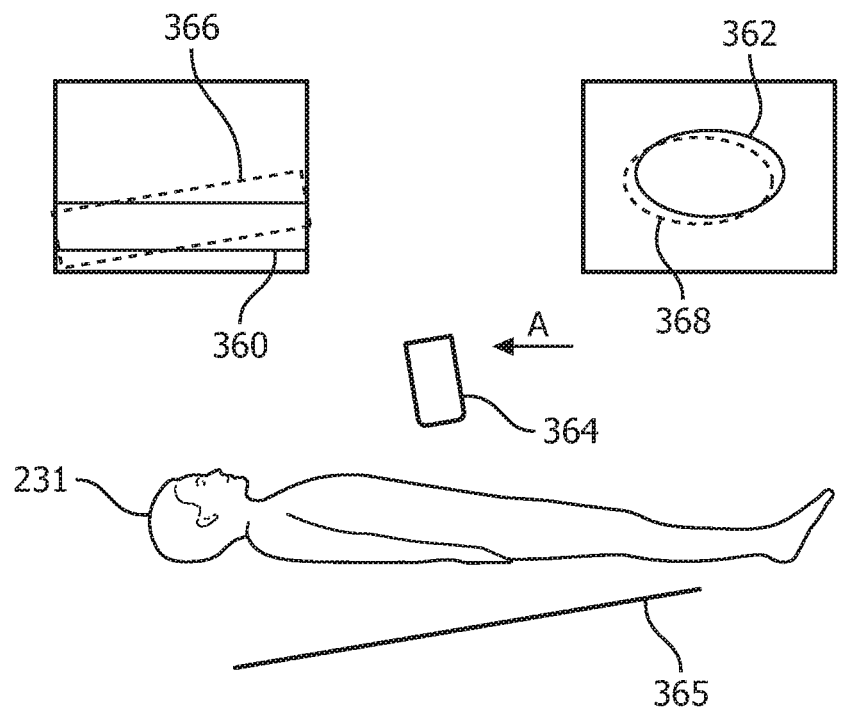
FIG. 4 is a diagram showing axial imaging planes with misalignment due to probe angle between live images taken by a first modality and static images taken by a second modality and further showing sagittal imaging planes aligned between live images taken by the first modality and static images taken by the second modality in accordance with the present principles.

Referring to FIG. 4, a diagram shows an example of plane alignment and error correction in accordance with one illustrative embodiment. Images 360 and 362 depict CT cross-sections taken axially (image 360) and perpendicularly to an axial direction (sagittal plane) (image 362) at a location on the patient 231. An ultrasonic probe 364 (e.g., a 3D electronic probe (134)) is employed to obtain an axial ultrasonic image 366 (dashed lines) and a sagittal ultrasonic image 368 (dashed lines) concurrently and in real-time.

As depicted, a slight tilt (arrow "A") along the axial direction results in the real-time image being misaligned in the axial direction (image 366 not aligned with image 360) and results in misalignment in the sagittal plane (images 368 and 362 are not aligned). The user can visually correct the misaligned images by moving the probe 364, which is also employed as an alignment mechanism, until the misalignment is removed (e.g., image 366 is aligned with image 360, and image 368 is aligned with image 362). A tilt 365 or other error is visualized and corrected immediately by angling the probe 364 until the axial planes and/or sagittal planes (or other planes) of the ultrasound and CT are aligned. For MR or CT acquisitions that are oblique, the angle of the oblique acquisition, e.g., stored in the DICOM header, could be read by the ultrasound or other real-time imaging system, and applied to the acquisition of the X-planes such that the X-planes have that same oblique angle applied.

It should be understood that other alignment mechanisms may be employed. For example, points may be selected using an interface that are common to the multiple planes. The common points may then be employed for visual alignment in the multiple planes.

Figure 5:
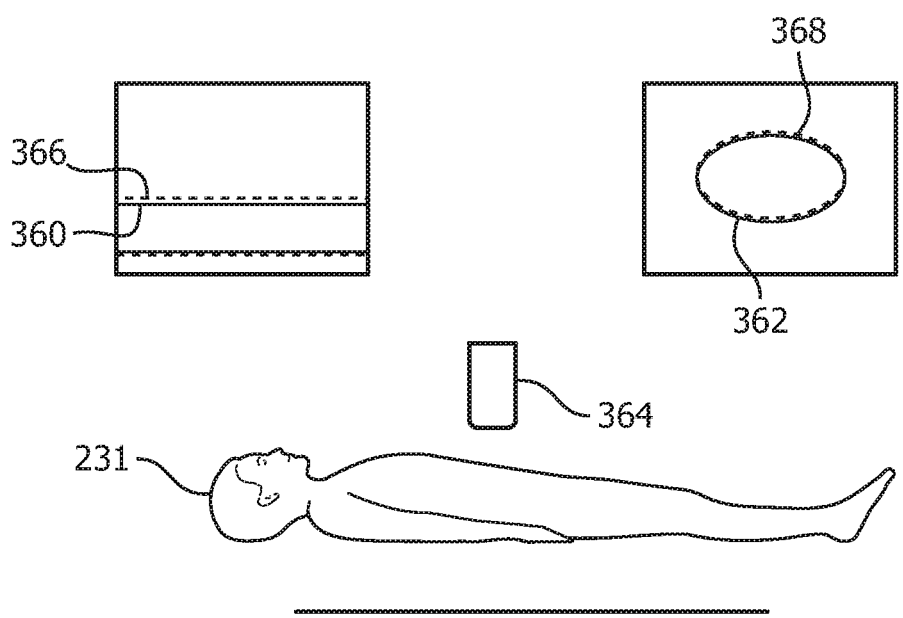
FIG. 5 is a diagram showing axial imaging planes and sagittal imaging planes in alignment due to reorientation of the probe and ready for registration in accordance with the present principles.

Referring to FIG. 5, correct alignment is achieved by moving the probe 364 (or other devices) to a position that achieves alignment in at least two planes between the ultrasonic images 366 and 368 and images 360 and 362, respectively. Once alignment is made in at least two directions/planes, e.g., axial and sagittal, axial, and coronal, sagittal and coronal or between any other planes, registration is locked in, and guidance or other operations may proceed using fused or registered data to ensure proper positioning and/or trajectories of medical instruments.

Figure 6:
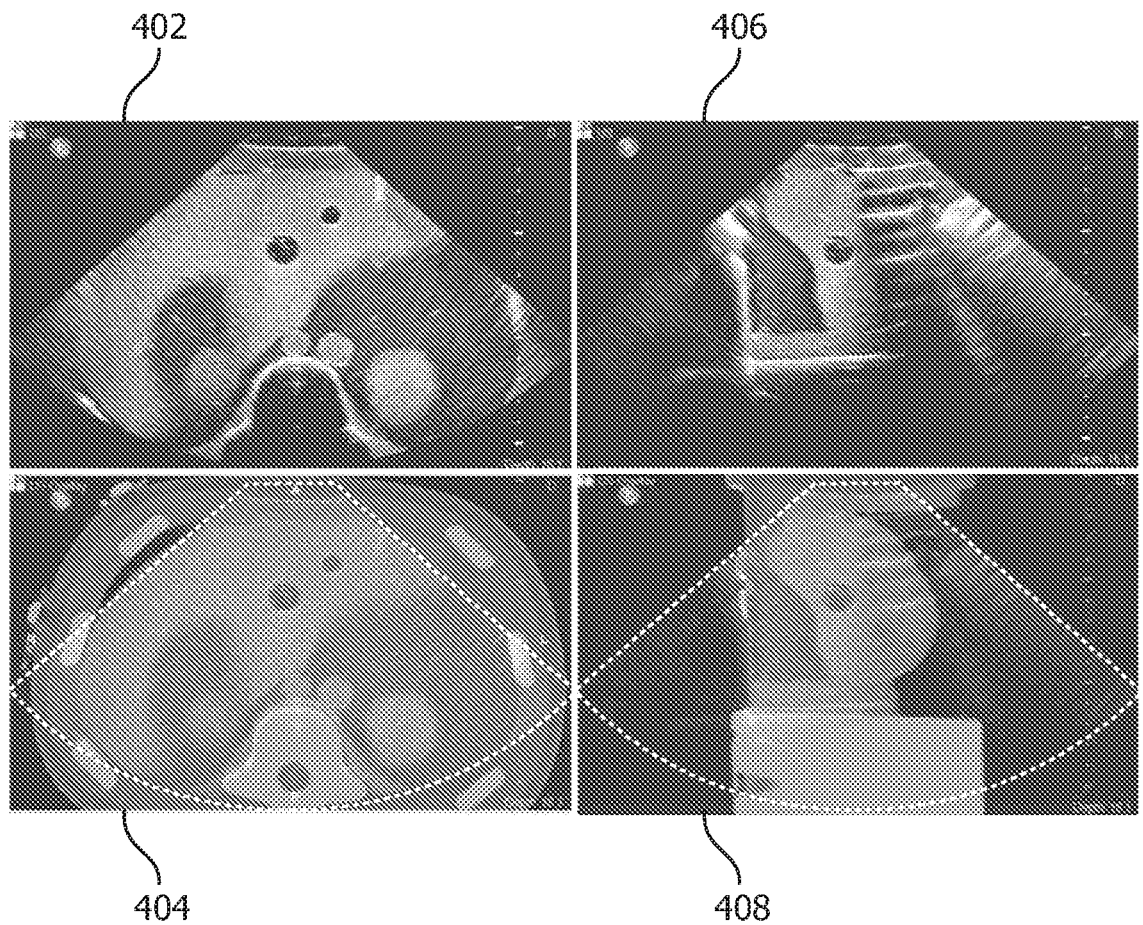
FIG. 6 shows a live image of an axial plane (upper left) provided by using an electronic 3D probe, and a same axial plane fused with an axial computed tomography (CT) slice (lower left), and upper and lower right images show a live sagittal plane and that same plane fused with a sagittal slice from CT in accordance with the present principles.

Referring to FIG. 6, example images 402, 404, 406 and 408 are illustratively shown. An upper left image 402 shows a live axial plane from an electronic 3D probe. A lower left image 404 shows the same axial plane fused with a CT image. An upper right image 406 and a lower right image 408 show the live sagittal plane and that same plane fused with the sagittal slice from the CT, respectively.

As shown, the system 100 (FIG. 1) displays live ultrasound images in two or more planes (e.g., both the axial plane and the sagittal plane). The CT or MR of the patient is displayed sliced also axially and sagittally and displayed with their respective ultrasound image. When the user identifies a common point in the axial ultrasound to axial CT (or sagittal ultrasound to sagittal CT), both the axial images are overlaid with each other, and both sagittal images are overlaid with each other. If the sagittal images demonstrate an offset or some angular rotation relative to each other, the user can immediately physically correct for that tilt before locking in that registration. It should be understood that the embodiments described may employ the use of additional planes including but not limited to a coronal plane, etc., in addition to other planes including intermediary planes.

Figure 7:
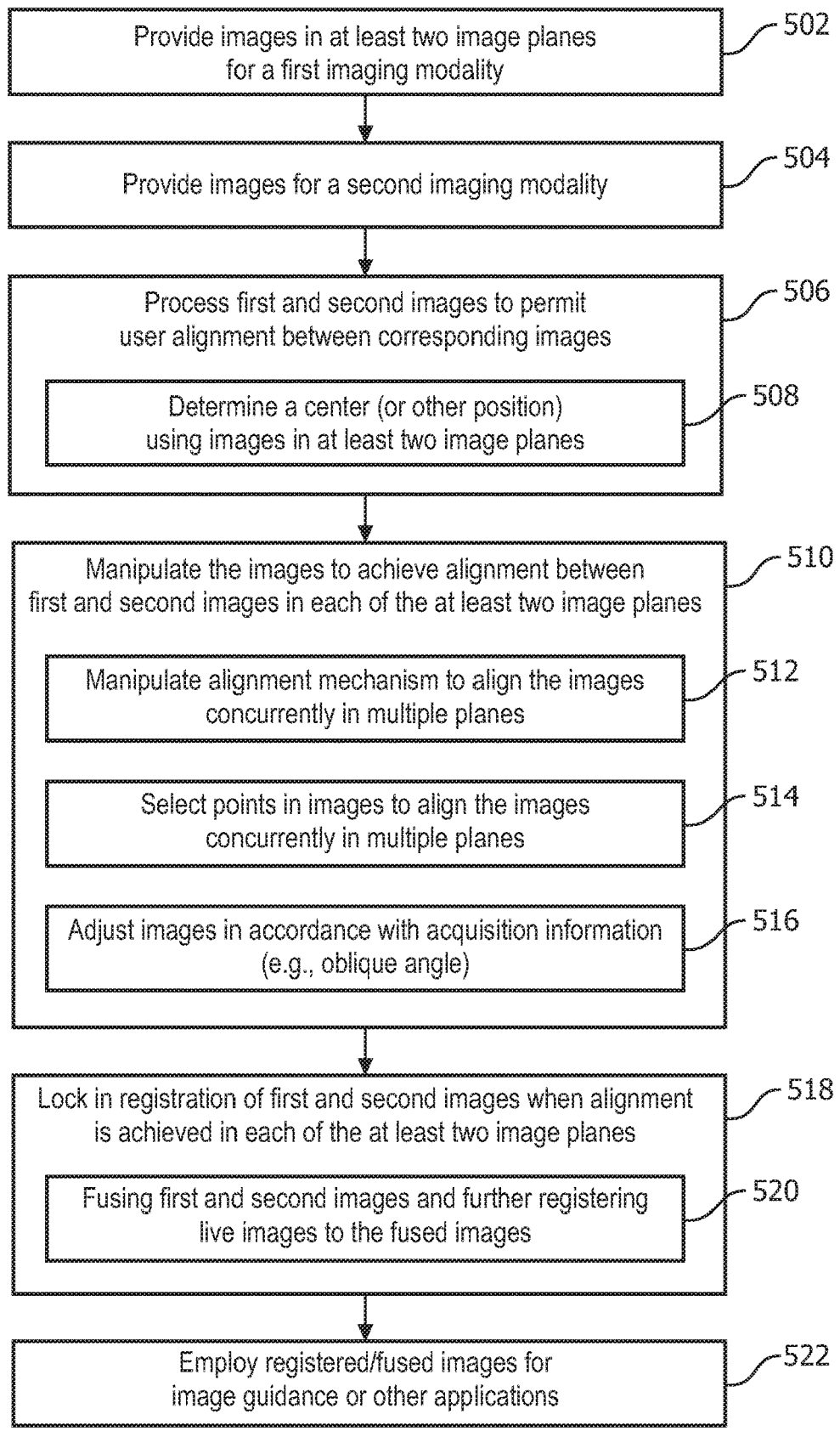
FIG. 7 is a flow diagram showing a method for image registration and device alignment in accordance with an illustrative embodiment.

Referring to FIG. 7, a method for image alignment, registration and device guidance is illustratively described in accordance with the present principles. In block 502, an imaging and alignment apparatus associated with a first imaging modality is positioned to concurrently provide images in at least two imaging planes for a subject. The first modality may include ultrasonic imaging, and the apparatus may include an integrated imaging mechanism and alignment mechanism, such as an electronic three-dimensional probe. In another embodiment, a three-dimensional (3D) image volume may be collected to generate the first images corresponding with imaging planes. In another embodiment, the apparatus includes an alignment mechanism that may include an interface (e.g., 120, FIG. 1) for assigning displayable points common to the at least two imaging planes. In block 504, second images are provided (e.g., generated or provided from memory) corresponding to the at least two imaging planes by reformatting a volume of image data acquired by a second imaging modality.

In block 506, first images are processed for the first imaging modality and second images collected are processed for the second imaging modality to permit user alignment between the first images and the second images in multiple planes. In block 508, processing may include determining a center (or other position) of a point of interest using images from multiple planes.

In block 510, the images are manipulated to achieve alignment between corresponding first and second images in the multiple planes. The alignment process is preferably visual and provided to the user on a display or displays. In block 512, the alignment can be performed by user manipulation of the alignment mechanism (e.g., probe) with visual feedback from one or more displays showing two or more planes. In one embodiment, alignment may be achieved by selecting points (e.g., using an interface) in the first images and/or the second images to concurrently align corresponding points in each of multiple image planes in block 514. Other alignment operations may include aligning reference line, aligning markers, etc. In block 516, the second modality may include computed tomography, magnetic resonance, etc. and processing may include adjusting the first modality images in accordance with an acquisition angle for the second images.

In block 518, registration between the first images with corresponding second images in the multiple planes is locked in when alignment in the multiple planes has been achieved. In block 520, registering may include fusing the first and second images and further registering live images to fused first and second images.

In block 522, the fused/registered images may be employed for device guidance or other applications. The multi-planar fused images may be employed to guide one or more instruments during a procedure. The image fusion/registration may be employed in image guided interventional procedures, e.g., PercuNav™. In one embodiment, device guidance and tissue characterization may be performed in accordance with FIG. 8.

Figure 8:
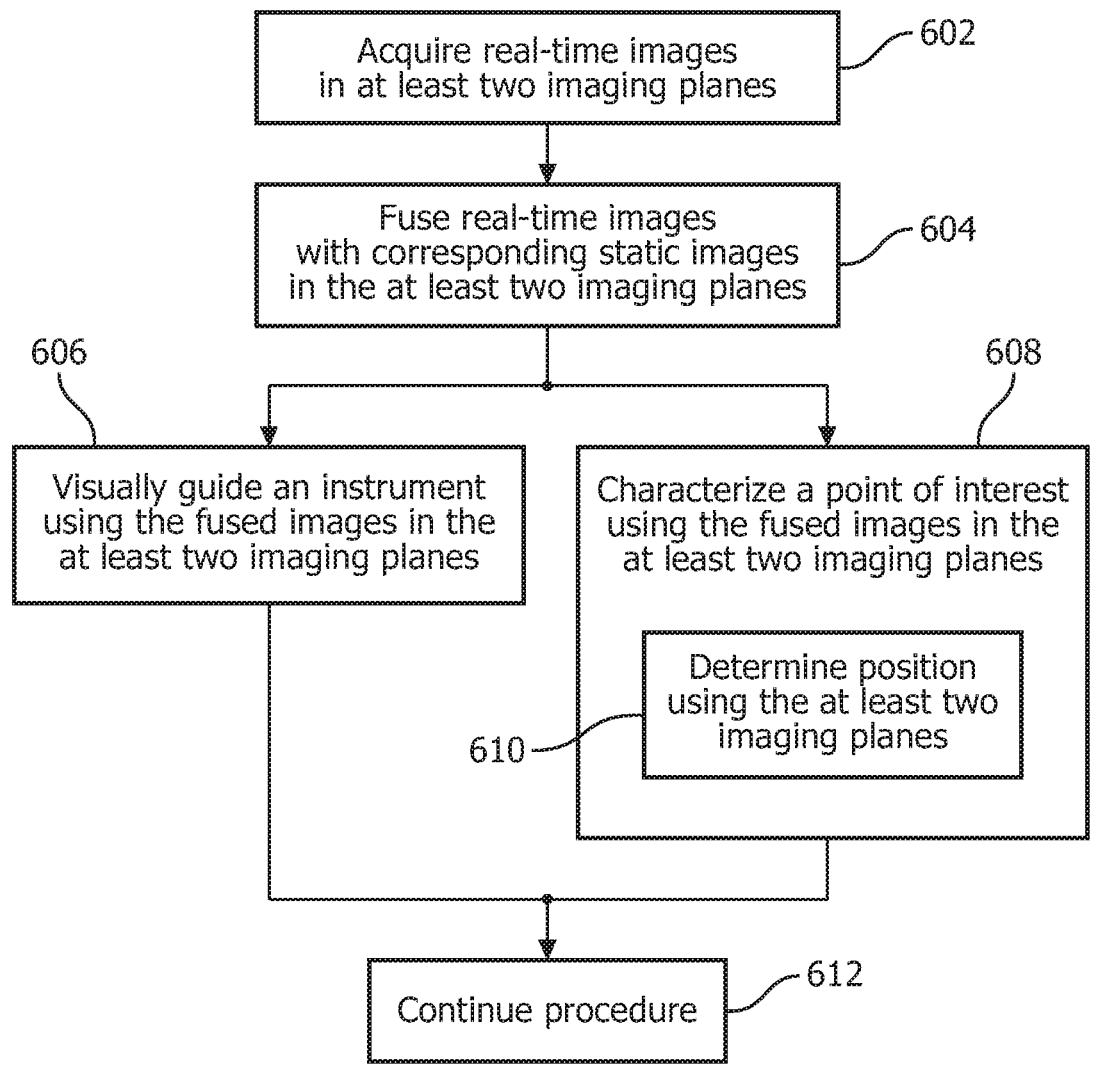
FIG. 8 is a flow diagram showing a method for device guidance in accordance with an illustrative embodiment.

Referring to FIG. 8, an illustrative method for instrument guidance and tissue characterization is shown. In block 602, real-time images are acquired with a first modality in at least two imaging planes. The first modality may include ultrasonic imaging, etc. The second modality may include one or more of computed tomography (CT), magnetic resonance (MR), positron emission tomography (PET), single photon emission computed tomography (SPECT), cone-beam CT, tomosynthesis, a stored ultrasound volume, etc.

In block 604, the real-time images are fused with second images collected with a second imaging modality that correspond to the real-time images in the at least two imaging planes to generate fused images. In one embodiment, fused images may be employed, and real-time images may be registered to the fused images. In block 606, an instrument is guided by concurrently visualizing the fused images in the at least two imaging planes to position the instrument during a procedure. The instrument may include a needle guided to a target, which is visualized in multiple planes. The multi-plane positioning ensures better accuracy and instills operator confidence in the device positioning process. In addition to or instead of instrument guidance, in block 608, a point or points of interest may be characterized in the fused images. The point of interest may include an anatomical feature, a lesion, tumor, tissue, etc. In block 610, the characterizing may include determining a center or other position on the point of interest using images from multiple planes. In block 612, the procedure is continued, as needed.

In interpreting the appended claims, it should be understood that:
 a) the word "comprising" does not exclude the presence of other elements or acts than those listed in a given claim;
 b) the word "a" or "an" preceding an element does not exclude the presence of a plurality of such elements;
 c) any reference signs in the claims do not limit their scope;
 d) several "means" may be represented by the same item or hardware or software implemented structure or function; and
 e) no specific sequence of acts is intended to be required unless specifically indicated.

Having described preferred embodiments for image registration and guidance using concurrent X-plane imaging with electronic probe (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system, comprising:
 an alignment mechanism configured to permit user alignment of images;
 an imaging mechanism associated with a first imaging modality, wherein the alignment mechanism and the imaging mechanism comprise an electronic three-dimensional probe,
  wherein the imaging mechanism is configured to concurrently provide at least two first images of a region of a subject in at least two different imaging planes, and
  wherein the imaging mechanism is associated with the alignment mechanism;
 an image processing module configured to concurrently display on a display the at least two first images, each of which shows a different one of the at least two different imaging planes,
 wherein the image processing module is configured to overlay the at least two first images with corresponding second images,
 wherein the corresponding second images are collected with a second imaging modality prior to the capture of the at least two first images and stored in a memory of the system, and
 wherein the image processing module is further configured to permit user alignment, using the alignment mechanism, between the at least two first images and the corresponding second images on the display when the at least two first images and the corresponding second images are concurrently displayed on the display, the alignment occurring in real time while the electronic three-dimensional probe is correspondingly moved; and
 a registration module stored in the memory of the system and configured to register the at least two first images with the corresponding second images in the at least two different imaging planes when alignment in the at least two different imaging planes has been achieved.

2. The system as recited in claim 1, wherein the first imaging modality comprises ultrasonic imaging, and wherein the second imaging modality is selected from the group consisting of computed tomography (CT), magnetic resonance (MR), positron emission tomography (PET), single photon emission computed tomography (SPECT), conebeam CT, tomosynthesis, or a stored ultrasound volume, and wherein the image processing module is configured to adjust live images corresponding to the at least two first images in accordance with an oblique acquisition angle for the second images.

3. The system as recited in claim 1, wherein the registration module is configured to fuse the first and second images for use in device guidance.

4. The system as recited in claim 1, wherein the alignment mechanism includes a user interface configured to allow a user to select points in at least one of the first images and the second images to concurrently align corresponding points in each of the at least two different imaging planes.

5. The system as recited in claim 1, wherein the system is configured to generate the first images corresponding with imaging planes of the second images from a three-dimensional (3D) image volume.

6. The system as recited in claim 1, wherein the image processing module is configured to determine a center of a point of interest from the at least two different imaging planes during instrument guidance.

7. The system as recited in claim 1, wherein the first images are taken in real-time by the first imaging modality and the second images are derived from static images.

8. The system as recited in claim 1, wherein the image processing module is configured to determine an acquisition angle of one of the second images, which is a static image, and make a correction to one of the first images, which is a live image, in accordance with the acquisition angle of the second static image.

9. A method, comprising:
positioning an electronic three-dimensional probe associated with a first imaging modality to concurrently provide two first images on a display in two different imaging planes for a region of a subject;
providing on the display, concurrently with the first images, two second images collected with a second imaging modality, wherein each of the two second images corresponds to one of the two first images which are in the two different imaging planes;
processing the two first images collected with the first imaging modality and the two second images collected with the second imaging modality to permit user alignment between each of the first images and the corresponding second images in the two different imaging planes on the display;
visually aligning the displayed first images and second images in the two different imaging planes by moving the two first images relative to the two second images while receiving user input corresponding to a user using the electronic three-dimensional probe as the two first images and the two second images are concurrently displayed on the display; and
locking in the alignment of the two first images with corresponding two second images in the two different imaging planes after visual alignment in the two different imaging planes has been achieved.

10. The method as recited in claim 9, wherein the first imaging modality includes ultrasonic imaging.

11. The method as recited in claim 9, wherein the second imaging modality is selected from the group consisting of computed tomography (CT), magnetic resonance (MR), positron emission tomography (PET), single photon emission computed tomography (SPECT), conebeam CT, tomosynthesis, or a stored ultrasound volume and processing includes adjusting the first modality images in accordance with an oblique acquisition angle for the second images.

12. The method as recited in claim 9, wherein visually aligning includes selecting points in the first images and the second images to concurrently align corresponding points in each of the two different imaging planes.

13. The method as recited in claim 9, wherein concurrently providing the two first images in the two different imaging planes includes collecting a three-dimensional (3D) image volume to generate the two first images corresponding with imaging planes of the second images.

14. The method as recited in claim 9, wherein locking in the alignment includes registering each of the two first images and the corresponding second images with each other.

15. The method of claim 9, wherein the two different imaging planes include two orthogonal planes.

16. The method of claim 15, wherein the two orthogonal planes are a sagittal plane and an axial plane.

17. A system, comprising:
a display;
an imaging mechanism associated with a first imaging modality, wherein the imaging mechanism is configured to concurrently provide image data for two first real-ti e images of a region of a subject in two corresponding orthogonal imaging planes;
a memory configured to store therein data for two second images of the region of a subject collected with a second imaging modality different from the first imaging modality prior to the two first real-time images, wherein the memory is further configured to store therein an image processing module configured to concurrently display on the display the two first real-time images overlaid with the two second images;
an alignment mechanism configured to be manipulated by a user, wherein the image processing module is further configured to align the two first real-time images and the two second images on the display in response to manipulation of the alignment mechanism by the user as the two first real-time images and the two second images are concurrently displayed on the display, the alignment mechanism and the imaging mechanism comprising an electronic three-dimensional probe, the alignment occurring in real time while the electronic three-dimensional probe is correspondingly moved; and
a registration module stored in the memory and configured to register the two first real-time images with the two second images in the two corresponding orthogonal imaging planes when alignment of the two first real-time images and the two second images in the two corresponding orthogonal imaging planes has been achieved.

18. The system of claim 17, wherein the two corresponding orthogonal imaging planes are a sagittal plane and an axial plane.

19. The system of claim 17, wherein the second imaging modality is selected from the group consisting of computed tomography (CT), magnetic resonance (MR), positron emission tomography (PET), single photon emission computed tomography (SPECT), cone-beam CT, and tomosynthesis.

* * * * *